United States Patent [19]
Tsilibary et al.

[11] Patent Number: 5,081,031
[45] Date of Patent: * Jan. 14, 1992

[54] SYNTHETIC POLYPEPTIDE WITH TYPE IV COLLAGEN ACTIVITY

[75] Inventors: Photini-Effie C. Tsilibary; Leo T. Furcht, both of Minneapolis, Minn.

[73] Assignee: Regents of the University of Minnesota, Minneapolis, Minn.

[*] Notice: The portion of the term of this patent subsequent to Oct. 24, 2006 has been disclaimed.

[21] Appl. No.: 450,629

[22] Filed: Dec. 14, 1989

[51] Int. Cl.$^5$ .................. C12M 1/00; C07K 7/08; A61F 2/02; A61F 2/06
[52] U.S. Cl. .................. 435/240.23; 435/284; 435/285; 435/301; 435/240.243; 530/327; 623/1; 623/6; 623/11; 623/22; 623/66
[58] Field of Search .................. 435/240.24, 240.241, 435/240.242, 240.243, 284, 285, 301, 240.23; 623/1, 6, 11, 22, 66; 530/327

[56] References Cited

U.S. PATENT DOCUMENTS

| | | | |
|---|---|---|---|
| 4,578,079 | 3/1986 | Ruoslahti et al. | 623/11 |
| 4,870,160 | 9/1989 | Charonis et al. | 623/1 |
| 4,876,332 | 10/1989 | Tsilibary et al. | 530/326 |

OTHER PUBLICATIONS

Koliakos et al., The Binding Of Heparin To Type IV Collagen: Domain Specificity With Identification Of Peptide Sequences From The α1 . . . , J. Biological Chemistry, vol. 264, No. 4, pp. 2313-2323, Feb. 5, 1989.
Herbst et al., Differential Effects Of Laminin, Intact Type IV Collagen, And Specific Domains Of Type IV Collagen . . . , J. Cell Biology, vol. 106, pp. 1365-1373, Apr. 1988.
Aumailley et al., Attachment Of Cells To Basement Membrane Collagen Type IV, J. Cell Biology, vol. 103, pp. 1569-1576, 1986.
R. Timpl et al., *Macromolecular Organization of Type IV Collagen,* in *New Trends in Basement Membrane Research,* Raven Press, NY at 57-67 (1982).
J. Murray et al., *J. Cell Biol.,* 80, 197-202 (1979).
M. Kurkinen et al., *J. Biol. Chem.,* 259, 5915-5922 (1984).
S. Sugrue, *J. Biol. Chem.,* 262, 3338-3343 (1987).
K. Tomaselli et al., *J. Cell Biol.,* 105, 2347-2358 (1987).
J. Oberbaumer et al., *Eur. J. Biochem.,* 147, 217-224 (1985).
T. Pihlajanien et al., *J. Biol. Chem.,* 260, 7681-7687 (1985).
U. Schwarz-Magdolen et al., *Febs. Lett.,* 208, 203-207 (1986).
D. Brazel et al., *Eur. J. Biochem.,* 172, 35-42 (1988).
R. Soininemi et al., *Febs. Lett.,* 225, 188-194 (1987).
D. Brazel et al., *Eur. J. Biochem.,* 168, 529-536 (1987).
G. Muthukamaran et al., *J. Biol. Chem.,* 264, 6310-6317 (1989).
J. Saus et al., *J. Biol. Chem.,* 264, 6318-6324 (1989).
W. Babel et al., *Eur. J. Biochem.,* 143, 545-556 (1984).
E. Tsilibary et al., *J. Cell Biol.,* 103, 2467-2473 (1986).
E. Tsilibary et al., *J. Biol. Chem.,* 263, 19112-19118 (1988).
M. Chelberg et al., *Cancer Research,* 49, 4796-4802 (1989).

*Primary Examiner*—Elizabeth C. Weimar
*Assistant Examiner*—George C. Elliott
*Attorney, Agent, or Firm*—Merchant, Gould, Smith, Edell, Welter & Schmidt

[57] ABSTRACT

A polypeptide having the following formula is provided: leu-ala-gly-ser-cys-leu-ala-arg-phe-ser-thr-met which can bind heparin and promote cellular adhesion. Medical devices such as prosthetic implants, percutaneous devices and cell culture substrates coated with a composition including the polypeptide are also provided.

14 Claims, 7 Drawing Sheets

FIG. 2

```
α1........MGPRLSVVLLLLFAALLLHEERSRAAAKGDCGGSG....CGKCDCHGVKGKGERGLPGLQGVIGPPGMQGPEGPHGPPGQKGDAGEPGLPG 88
           ||  ||||     |       |      |     |||  ||  |  | ||  || ||  |  | ||| ||| |
α2MDRVRPKASGPPLRGWLLLATVTVGLLAQSVLGGVKKLDVPCCGRDCSGGCQCYPEKGARGQPGAVGPQGYMGPPGLQGPPGLQGRKGDKGERGVPGPTG 100

TKGTRGPPGAAGYPGNPGLPGIPGQDGPPGPPGIPGCMGTKGERGPLGPPGLPGPSGNPGPPGLPGMKGDPGEILGHVPGTLLKGERGFPGIPGMPGSPG 188
     ||   |   |||  |  ||| || ||   ||||||  |  ||| ||||||||| |||| |   I      ||| |||  ||
PKGDVGARGVSGFPGADGIPGHPGQGGPRGRPGYDGCMGTRGDAGPQGPSGSGGPPGLPGPQGPKGQKGEPYALSKEDRDK.YRGEPGEPGLVGYQGPPG 199

LPGLQGPVGPPGFTGPPGPPGPPGEKGQMGSSFQGPKGDKGEQGVSGPPGVPGQAQVKEKGDFAP.....TGEKGQKGEPGFPGVPGYGEKGEPGKQ 283
||  | | |||||||||||| | |  III|| ||  |||| |||       III    |||| || | ||||IV|| |  |
RPGPIGQMGPMGAPGRPGPPGPPGPKGQPGMRGLGFYGQKGERGDIGQPGPMGIPSDITLVGPTTSTIHPDLYKGERGDEGEQGIPGVISKGEEGIMGFP 299

GPRGKPGKDGEKGERGSPGIPGDSGYPGLPGRQGPQGEKGEAGLPGPPGPGTVIGTMPLGEKGDRGYPGAPGLRGEPGPKGFPGTPGQPGPPGFPTPGQAGA 383
|||| |||||   | |  || |   | || || || |||| ||||  |V| | |||| || |  ||||  ||| |||| VI
GIRGFPGLDGEKGVVGQKGSRGLDGFQGPSGPRGPKGERGEQGPPGPS..VYSPHPSLAKGARGDPGFQGAHGEPGSRGEPGEPGTAGPPGPSVGDEDSM 397

PGFPGERGEKGDQGFPGVSLP..GPSGRDGAPGPPGPPGPPGQPGHTNGIVECQPGPPGDQGPPGTPGQPGLTGEVGQKGQKGESCLACDTEGLRGPPGP 481
  |||| ||  || VII|||  || ||||| |||  || VIII    |  |  |||  |  |||||||  IX    | ||
RGLPGEMGPKGPFSGEPGSPARYLGPPGADGRPGPQGVPGPAGPPGPDGFLF....GLKGSEGRVGYPGPSGFPGTRGQKGWKGEAGDCQCGQVIGGLPGL 493

QGPPGEIGFPGQPGAKGDRGLPGRDGLEGLPGPQGSPGLIGQPGAKGEPGEIFFDMRLKGDKGDPGFPGQPGMPGRAGTPGRDGHPGLPGPKGSPGS..I 579
  ||| |  |  | ||| || |   ||| || || ||| ||  | |||   X  ||  || || | |||||  |||  || ||  | ||XI
PGPKGFPGVNGELGKKGDQGDPGLMKIPGFPGFKGAPGVAGAPGPKGIKGDS.RTITTKGERGQPGIPGVHGMKGDDGVPGRDGLDGFPGLPGPPGDGIK 592

GLKGERGPPGGVGFPGSRGDIGPPGPPGPVGPIGPVGEKGQAGFPGGPGSPGLPGPKGEAG.................KVVPLPGPPGAAGLPGSPGF 659
   |  || |  |||||| XII|| |   ||| | |||||||| |  |     XIII                |||  |  ||||
GPPGDAGLPGVPGTKGFPGDIGPPGQGLPGPKGERRGFPGDAGLPGPPGFPGPPGPPGPPGPGTPGQRDCDTGVKRPIGGGQQVVVQPGCIEGPTGSPGQPGPPGP 692

PGPQGDRGFPGCTPGRPGIPGEKGAVGQPG.IGFPGLPGPKGVDGLPGEIGRPGSPGRPGFMGLPGMPGPQGQMGEPGIGL...PGLKGQPGLPGIPGTPG 755
 | || |||  | ||    |||  |||||XIV||||  |  |  |  | |  | || |  ||||   ||| | |XV ||  |   ||| ||  |
TGAKGVRGHPGFPGASGEQGLKGFPGCDPGREGFPGPPGFMGPRGSKGTTGLPGPDGPPGPIGLPGPAGPPGDRGIPGEVLGAQPGTRGDAGLPGQPGLKG 792

EKGSIGGPGVPGEQGLTGPPGLQGIRGDPGPPGVQGPAGPPGVPGI.GPPGAMGPPGGEGPPGSSGPPGIKGEKGFPGPPG.LDMPGPKGDKGSQGLPGL 853
  || | || |||  |  ||||| |  || || |  |||| XVI||   ||  ||  ||  ||| || ||XVII | ||| | ||
LPGETGAPGFRGSQGMPGMPGLKGQPGCFPGPSGQPGQSGPPGQHAFPGTPGREGPLGQPGSPGLGGLPGDRGEPGDPGVPGVGMKGLSGDRGDAGMSGE 892

TGQSGLPGLPGQQGTPGVPGFPGSKGEMGVMGTPGQPGSPGPAGTPGLPGEKGDMGLPGSSGPRGDPGFKGDKGDVGLPGMPGSMEHVDMGSMKGQKGDQ 953
 | |||  ||||||||||  ||||||  || |  | |||  |||   ||||| | || |   ||||||| ||||| ||||XVIII|  || |||
RGHPGSPGFKGMAGMPGIPGQKGDRGSPGMDGFQGMLGLKGRQGFPGTKGEAGPFFGVPGLKGLPGEPGVKGNRGDRGPPG..PPPLILPGMKDIKGEKGDE 991
```

FIG. 2 CONTINUED

```
GEKGQIGPTGDKGSRGDPGTPGVPGKDGQAGHPG.QPGPKGDPGLSGTPGSPGLPGPKGSVGGMGLPGSPGEKGVPGIPGSQGVPGSPGEKGAKGEKGQS 1052
 |  |   |  ||  | ||  |||  |   |  |||XIX|  |||  |  ||||  || ||   |   |  ||    |   |  ||   |||  |   |  |  |
GPMGLKGYLGLKGIQGMPGVPGVSGPPGLPGRPGPIKGVRGDIGVPGTPGLPGFPGVSGPPGITGPPGPTGSRGEKGTPGVAGVFGETGPTGDPGDIGD. 1090

GLPGIGIPGRPGDKGDQGLAGFPGSPGEKGEKGSAGTPGMPGSPGPRGSPGNIGHPGSPGLPGEKGDKGLPGLDGVPGVKGEAGLPGTPGPTGPAGQKGE 1152
XX   |||  |   |  |   |  ||||    |  ||  |  ||||  |  |||| |  ||    || ||   | ||  ||  |  |  |  |
TVDLPGSPGLKGERGITGIPGLKGFPGEKGAAGDIGPPGITGMAGAQGSPGLKGQTGFPGLTGLQGPQGEPGRIGIPGDKGDPGWPGVPGLPGFPGIRGI 1190

PGSDGIPGSAGEKGEQGVPGRGFPGFPGSKGDKGSKGEVGFPGLAGSPGIPGVKGEQGFMGPPGPQGQPGLPGTPGHP....VEGPKGDRGPQGQPGLPG 1248
 | |||  |  |  ||XXI| |||||  ||| |  ||XXII | |  | || |||  |  || |||| | || XXIII  |  |||  |  ||| |
SGLHGLPGTKGFPGSPGVDAHGDPGFPGPTGDRGDRGEAN..TLPGPVGVPGQKGERGTPGERGPAGSPGLQGFPGISPPSNISGSPGDVGAPGIFGLQG 1288

HPGPHGPPGFPGINGPKGDKGNQGWPGAPGVPGPKGDPGFQGMPGIGGSPGITGSKGDMGLPGVPGFPGQGQKGLPGLQGVKGDQGDQGVPGPKGLQGPPGP 1348
 || |||||XXIV | |||  |  |  |  | |||| ||  |  ||  |  | || |  |  |  |   |  ||  | |||||  |||  |  |  ||
YQGPPGPPGPNALPGIKGDEGSSGAAGFPGQKGWVGDPGPQGQPGVLGLPGERGPKGEQGFMGNTGPSGAVGDRGPKGPKGDQGFPGAPGSNGSPGIPGI 1388

PGPYQVIKGEPGLPGPEGPPGLKGLQGPPGPKGQQGVTGSVGLPGPPGVPGFDGAPGQKGETGPPGPPGPGRGFPGPPGPDGLPGSNGPPKPPSVDHGFLV 1448
|XXV | |  |  | ||| |  || ||| |  |  | ||| |XXVI|| | ||| || | || || | || || ||   || ||
PQKIAVQPGTLGPQGRRGLPGALGEIGPQGPPGDPGFRGAPGKAGPQGRGGVSAVPGFRGDQGPMGHQGPVGQEGEPGRPGSPGLPGMRG.RSVSIGYLL 1487

TRHSQTTDDPLCPPGTKILYHGYSLLYVQGNERAHGQDLGTAGSCLRKFSTMPFLFCMINNVCNFASRMDYSYWLSTPEPMPMSHAPISGDWIRPFISRC 1548
||||   | ||| |  |  ||||||| | || |||| |||||||||| |||||| |||||| || ||  |||||| | | ||   |  ||||
VKHSQTDQEPMCPVGMNKLWSGYSLLYPEGQEKAHNQDLGLAGSCLARFSTMPFLYCMPGDVCTYASRNDKSYWLSTTAPLP..MMPVAEEEIKPYISRC 1585

AVCEAPAMVMAVHSQTIQIPQCPNGWSSLWIGYSFVMHTSAGAEGSGQALASPGSCLEEFRSAPFIECH.GRGTCNYYAMAYSFWLATIERSEMFKKPTP 1647
||||||  |||||  ||  |  ||||||||  | ||  |  |  |||||||||  |||||||| ||  ||||| | ||||||||||||| ||
SVCEAPAVAIAVHSQDTSIPHCPAGWRSLWIGYSFLMYTAAGDEGGGQSLVSPGSCLEDFRATPPFIECNGGRGTCHYPAMKYSFWLTTIPEQNFQSTPSA 1685

STLKAGELRTHVSRCQVCMRRT 1669
|||||  ||  |||||||||
DTLKAGLIRTHISRCQVCMKNL 1707
```

SYNTHETIC POLYPEPTIDE WITH TYPE IV COLLAGEN ACTIVITY

GOVERNMENT SUPPORT

This invention was made with government support under contract No. DK 39216-02 by the U.S. Institutes of Health. The government has certain rights in the invention.

BACKGROUND OF THE INVENTION

Type IV collagen is a distinctive glycoprotein which occurs almost exclusively in basement membranes, structures which are found in the basal surface of many cell types, including vascular endothelial cells, epithelial cells, etc. Type IV collagen is a major component of basement membranes. It differs from interstitial collagens. See *New Trends in Basement Membrane Research*, K. Kuehn et al., eds., Raven Press, NY, at pp. 57–67 (1982). Type IV collagen has a molecular weight (MW) of about 500,000 and consists of three polypeptide chains: two α1 (MW 185,000) chains and one α2 (MW 170,000) chain. Type IV collagen has two major proteolytic domains: a large, globular, non-collagenous, NCl domain and another major triple-helical collagenous domain. The latter domain is often interrupted by non-collagenous sequences of variable length. A diagrammatic representation of the type IV collagen molecule is shown in FIG. 1. It is a complex and multidomain protein with different biological activities residing in different domains.

Type IV collagen self-assembles to polymeric structures which constitute the supportive frame of basement membranes. Various other macromolecular components bind to type IV collagen, such as: laminin, entactin/nidogen and heparan sulfate proteoglycan. An additional function of type IV collagen is to mediate cell binding. A variety of cell types specifically adhere and spread onto type IV collagen-coated substrata. See J. C. Murray et al., *J. Cell Biol.*, 80, 197–202 (1979); M. Aumailley et al., *J. Cell Biol.*, 103, 1569–1576 (1986); T. J. Herbst et al., *J. Cell Biol.*, 106, 1365–1373 (1988). Various cell surface proteins, a 47 kD protein [M. Kurkinen et al., *J. Biol. Chem.*, 259, 5915–5922 (1984)], a 70 kD protein [S. P. Sugrue, *J. Biol. Chem.*, 262, 3338–3343 (1987)] and members of the superfamily of integrins [K. J. Tomaselli et al., *J. Cell Biol.*, 105, 2347–2358 (1987)], have been reported to mediate cell binding to type IV collagen.

The variety of functions of type IV collagen suggests that this glycoprotein is important in many diverse and clinically relevant processes such as cell attachment and migration, wound healing, tumor cell metastasis and invasion, diabetic microangiopathy, vascular hypertrophy due to hypertension and several kidney diseases such as diabetic nephropathy and nephrotic syndromes of variable etiology. For example, in Goodpasture's syndrome, a disease characterized by hemoptysis and hematuria due to alveolitis and nephritis, respectively, an antibody to the major noncollagenous NCl domain of type IV collagen is found in the serum of all Goodpasture's patients. Another hereditary kidney disease, Alport's familial nephritis, is apparently due to a genetic defect of the NCl domain of type IV collagen. In addition, in diabetes mellitus, intact type IV collagen, as well as the triple helix-rich domain, are chemically modified and functionally impaired by the increased amounts of glucose present in the plasma and in the immediate vicinity of the basement membranes, i.e., in the extracellular matrix.

In order to better understand the pathophysiology of these processes at a molecular level, there is a need to try to assign at least several of the above-mentioned biological activities of type IV collagen to the specific proteolytic domains (i.e., NCl, triple helix-rich domains) or oligopeptide of type IV collagen. If this can be achieved, it will be possible to synthesize small peptides which can provide the basis for important pharmaceutical compositions.

BRIEF DESCRIPTION OF THE INVENTION

The present invention provides a polypeptide (hereinafter designated "Hep-II") which represents a fragment of the α2 chain of type IV collagen. This polypeptide can be prepared by conventional solid phase synthesis. The formula of the polypeptide is:

leu-ala-gly-ser-cys-leu-ala-arg-phe-ser-thr-met

Polypeptide Hep-II formally represents isolated type IV collagen residues 49–60 from the carboxyl-terminus of the α2 chain of the NCl domain of type IV collagen. The single letter amino acid code for this polypeptide is LAGSCLARFSTM.

This synthetic polypeptide was assayed for biological activity and found to be an extremely potent promoter of heparin-binding to synthetic substrates. Polypeptide Hep-II was also a potent promoter of cell adhesion and spreading of many cell types, including melanoma and endothelial cells. Therefore, it is believed that polypeptide Hep-II may be useful to (a) promote cellular attachment to culture substrata, (b) inhibit the metastasis and invasion of malignant cells, and (c) promote wound healing and implant acceptance. Since other cell types have been shown or are expected to have similar behavior in response to Hep-II, other uses of peptide Hep-II can be envisioned, such as assistance in nerve regeneration. Furthermore, since it is expected that further digestion/hydrolysis of peptide Hep-II in vitro or in vivo will yield some fragments of substantially equivalent bioactivity, such lower molecular weight peptides are also considered to be within the scope of the present invention.

BRIEF DESCRIPTION OF THE DRAWINGS

FIG. 2 depicts the primary amino acid sequence of the α1 and α2 chains of type IV collagen in comparison.

DETAILED DESCRIPTION OF THE INVENTION

Figure 1:
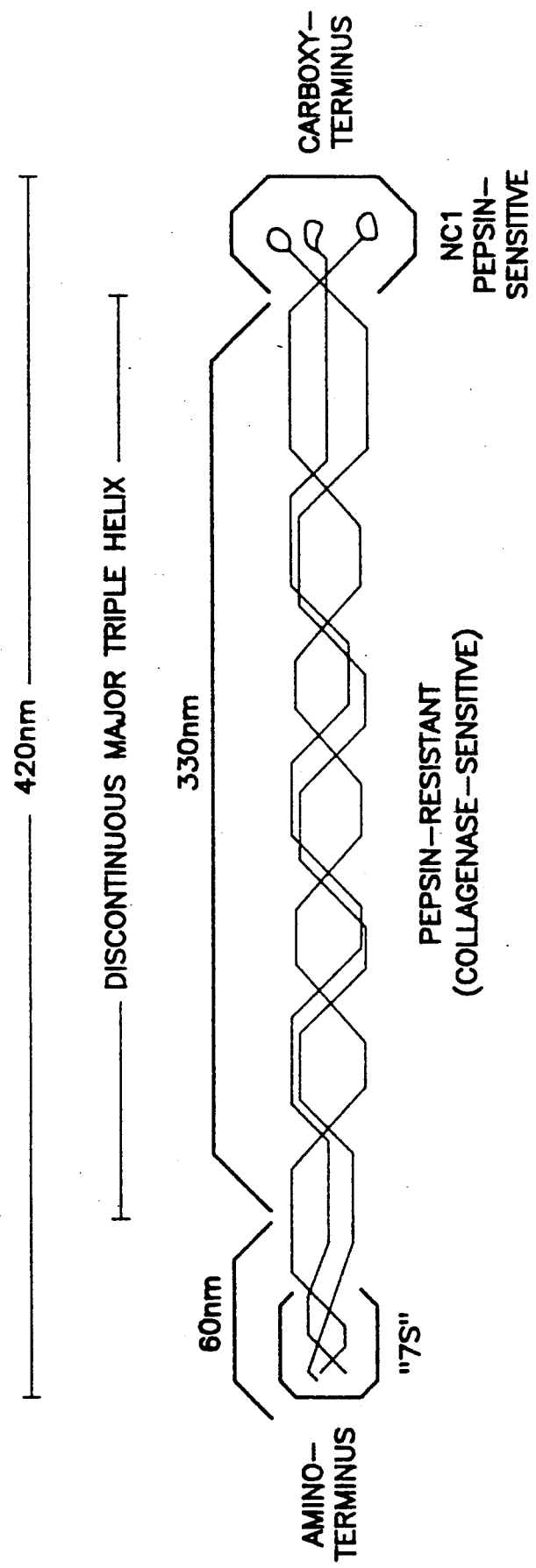
FIG. 1 is a diagrammatic representation of type IV collagen, indicating the structure of the α1(IV) and α2(IV) chains, each with a major non-collagenous, NCl domain and the triple helix-rich domain containing interruption of the gly-X-Y triple helical motif.

The structure of the two chains, the $\alpha 1$ and $\alpha 2$ chains of type IV collagen, has been the subject of much study. See J. Oberbaümer et al., *Eur. J. Biochem.*, 147, 217-224 (1985); T. Pihlajanien et al., *J. Biol. Chem.*, 260, 224 (1985); T. Pihlajanien et al., *J. Biol. Chem.*, 260, 7681-7687 (1985): U. Schwarz-Magdolen et al., *Febs. Lett.*, 208, 203-207 (1986); D. Brazel et al., *Eur. J. Biochem.*, 172, 35-42 (1988); R. Soininemi et al., *Febs. Lett.*, 225, 188-194 (1987); D. Brazel et al., *Eur. J. Biochem.*, 168, 529-536 (1987); G. Muthukamaran et al., *J. Biol. Chem.*, 264, 6310-6317 (1989); J. Saus et al., *J. Biol. Chem.*, 264, 6318-6324 (1989). The sequence of the $\alpha 2$ chain is shown in FIG. 2. Two copies of the $\alpha 1$ chain and one copy of the $\alpha 2$ chain are put together to make up the type IV collagen molecule. The total number of amino acids per collagen molecule is approximately 4,550. The $\alpha 2$(IV) chain contains about 1,707 amino acids.

Binding sites for heparin are of special interest since heparin-related macromolecules such as heparan sulfate proteoglycans are present in basement membranes and cell surfaces as well. Therefore, the association of these heparin-related molecules with type IV collagen may affect basement membrane structure and various cellular functions (such as adhesion, motility/migration, spreading, etc.).

As described in our U.S. Pat. No. 4,876,332, we observed that a peptide from the NC1 domain of the $\alpha 1$-(IV) chain of type IV collagen had the ability to bind heparin and promote cell adhesion. This peptide had the following sequence: thr-ala-gly-ser-cys-leu-arg-lys-phe-ser-thr-met, or TAGSCLRKFSTM based on the single letter code. This peptide, named TS-2, or peptide Hep-I corresponded to amino acid position 49-60 from the carboxyl terminus of the $\alpha 1$ (NCl) chain. Peptide Hep-II described herein binds to heparin approximately 10 times stronger than peptide Hep-I and is also a potent promoter of cell attachment and spreading.

Synthesis of the Polypeptide

The polypeptide of the invention was synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. (2nd ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxycarbonyl (BOC) group is used to protect the free amino group of the amino acid. This protecting group is removed with 25% trifluoroacetic acid (TFA) in dichloromethane (DCM). The newly exposed amino group is converted to the free base by 10% triethylamine (TEA) in DCM. The next BOC-protected amino acid is then coupled to the free amino of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using a 1.0 M acetic acid, followed by lyophilization of the extract. Lyophilized crude polypeptides are purified by preparative high performance liquid chromatography (HPLC) by reverse phase technique on a C-18 column. A typical elution gradient is 0% to 60% acetonitrile with 0.1% TFA in H$_2$O. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6 M HCl (constant boiling) or in 4 N methanesulfonic acid, when cysteine or tryptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The invention will be further described by reference to the following detailed examples.

EXAMPLE 1 Heparin Binding to Plastic Plates Coated With Peptide Hep-II

Figure 3A:
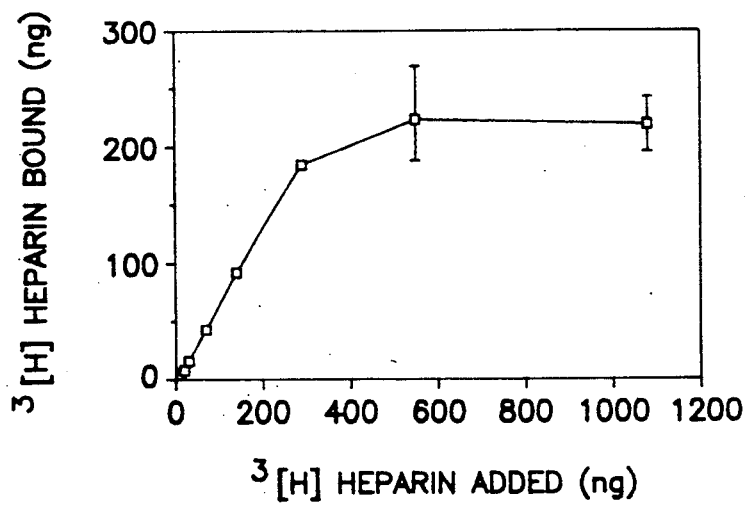
FIG. 3A is a graph showing the direct binding of increasing concentrations of heparin to peptide Hep-II coated on plastic substrates.
Figure 3B:
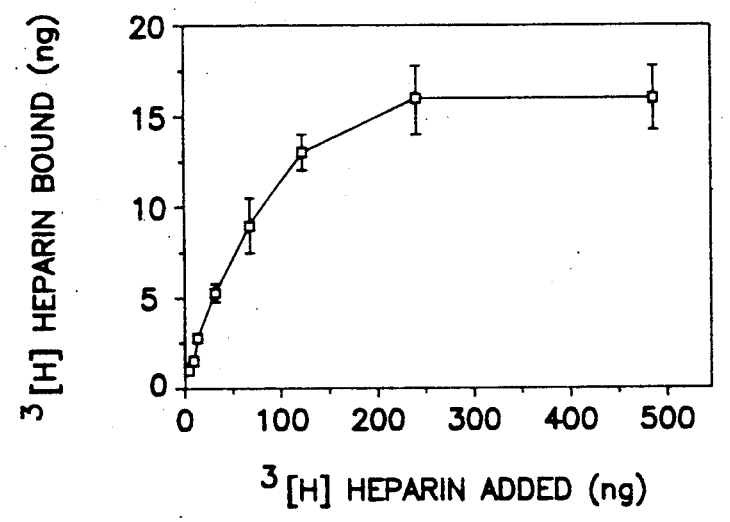
FIG. 3B is a graph showing the direct binding of increasing concentrations of heparin to peptide Hep-I coated on plastic substrates.
Figure 3C:
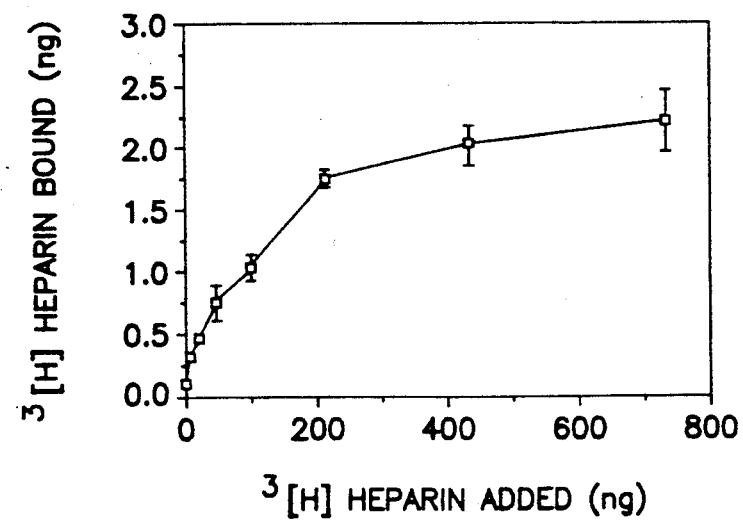
FIG. 3C is a graph showing the direct binding of increasing concentrations of heparin to type IV collagen coated on plastic substrates.

The ability of the synthesized peptide Hep-II to interact with heparin when coated on 96-well plastic plates was evaluated. Stock solutions of peptide Hep-II at a concentration of 500 $\mu$g/ml were prepared in phosphate-buffered saline containing 0.02% sodium azide. Fifty $\mu$l from each concentration was coated on the 96-well plates and left to dry overnight at 28° C. Then, wells were treated for two hours with 200 ml of 2 mg/ml BSA and 6 mM phosphate, 10 mM NaCl, 68 μM $CaCl_2$, pH 6.8 (wash buffer) in order to minimize non-specific binding. Next 50 μl of $^3$H-heparin (10 μg/ml) was added at increasing concentrations (0 to 1400 ng/well) for two hours at 37° C. The wells were then washed three times with wash buffer containing 0.05% Triton X-100 and finally they were incubated for thirty minutes at 60° C. with 200 μl of 0.5 N NaOH and 1% SDS. The amount of $^3$H-heparin bound at each concentration was quantitated with a Beckman LS-3801 liquid scintillation counter. The results shown in FIG. 3 indicate that peptide Hep-II is a very potent binder of heparin. Comparison with data obtained in the past using exactly the same methodology indicate that peptide Hep-II is at least 10 times stronger than peptide Hep-I (see FIG. 3B) and about 100 times stronger than type IV collagen, when used in the same coating concentrations. See FIG. 3C.

EXAMPLE 2 Inhibition of Heparin Binding to Type IV Collagen by Peptide Hep-II

Figure 4:
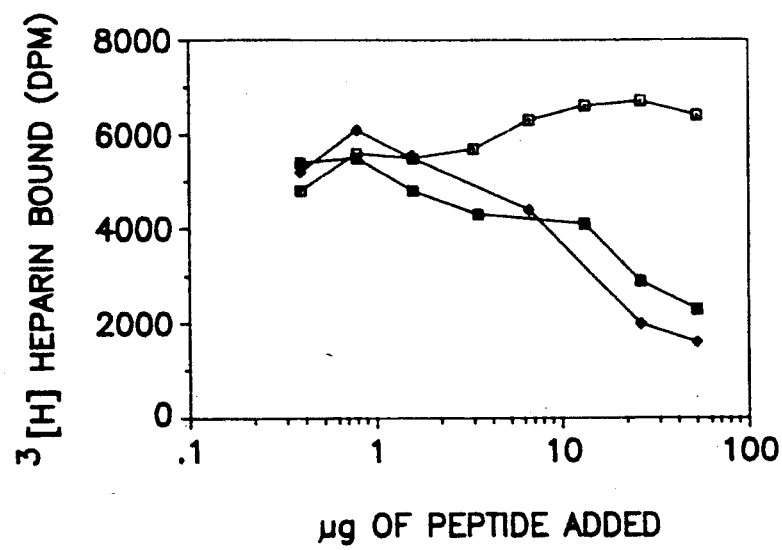
FIG. 4 is a graph showing the inhibition of the binding of heparin to the triple helix-rich domain of type IV collagen, by increasing concentrations of peptide Hep-II (♦) and Hep-I (■) previously referred to as: TS-2 in U.S. Pat. No. 4,876,332) or control peptide 1 (◨) present in solution.

Peptide Hep-II in solution (and not absorbed to plastic), was screened for the ability to inhibit the binding of heparin to intact, native type IV collagen coated on plastic. This experimental approach avoids problems due to differential coating of peptides in heparin binding assays. Type IV collagen at 60 μg/ml in PBS was coated on 96-well plates, using 50 μl per well and dried overnight at 28° C. The wells were then treated for two hours with 2 mg/ml BSA in wash buffer (described above in Example 1). Peptide Hep-II at various dilutions ranging from 0.5 mg/ml to 5 μg/ml in PBS and CHAPS (cholamido-propyl-dimethyl-ammonio-propane-sulfonate) (a detergent used to avoid non-specific sticking) was co-incubated with a standard amount of $^3$H-heparin (500 ng per well 50 μg/ml final concentration) for two hours at 37° C. and the mixture was then transferred to the laminin coated plate (50 μl ) and allowed to incubate for another two hours at 37° C. The wells were then washed and radioactivity was counted as described above. The results shown in FIG. 4 indicate that peptide Hep-II is a strong inhibitor of heparin binding to type IV collagen. Peptide Hep-I is also shown in comparison. These results also suggest that peptide Hep-II can bind to heparin not only when coated on plastic, but also when present in solution. Another control peptide (peptide 1 formula NPLCPPGTKIL) of similar length and hydropathy index, when tested with this assay was unable to compete for the binding of heparin to type IV collagen-coated plastic (FIG. 4).

EXAMPLE 3 Heparin/Peptide Interaction Specificity

Figure 5:
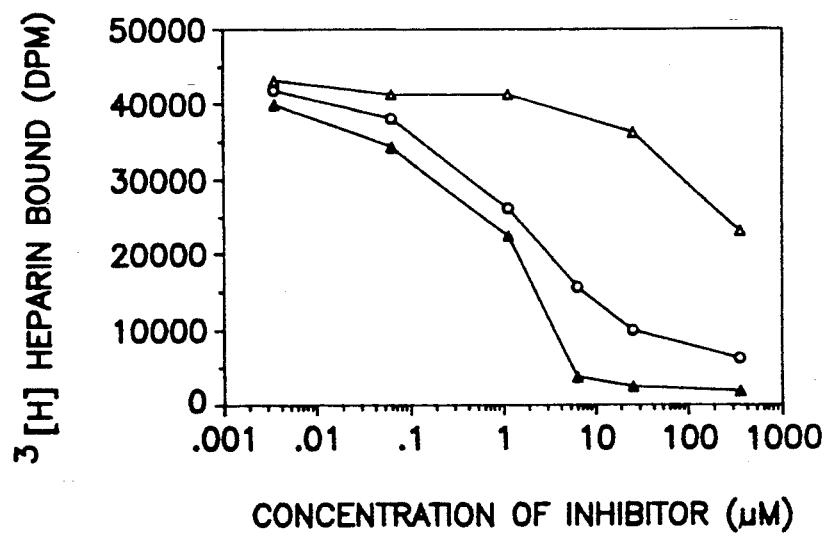
FIG. 5 is a graph depicting the competition of the binding of heparin to peptide Hep-II coated on plastic by various glycosoaminoglycans [heparin (▲), dextran (○) and chondroitin (△)] at increasing concentrations.

To check the specificity of the interaction between heparin and peptide Hep-II or whether the heparin structure was also critical to this interaction, heparin along with other sulfated glucosaminoglycans, dextran and chondroitin sulfate were used in competition experiments. A standard amount of 50 μg of a solution containing 500 μg/ml of peptide Hep-II was coated on 96-well plates as described above. Wells were treated for two hours with 2 mg/ml BSA in wash buffer. Then, a final volume of 50 μl was added to each well, containing a standard amount of $^3$-heparin (50,000 cpm per well) and various amounts of non-radioactive heparin, dextran or chondroitin sulfate. After incubating for two hours at 37° C., the wells were washed and radioactivity was counted as described above in Example 1. FIG. 5 shows that unlabeled heparin is able to compete for the binding of tritiated heparin to peptide Hep-II at very low concentrations, whereas substantially more dextran is needed to achieve similar levels of competition and chondroitin sulfate cannot mimic this effect except at extremely high concentrations. These results suggest that not only the charge, but also the conformation of the glycosaminoglycan is crucial for this interaction.

EXAMPLE 4 Effect of Peptide Hep-II in the Adhesion of Endothelial Cells

A. Isolation of Bovine Aortic Endothelial Cells

Figure 6:
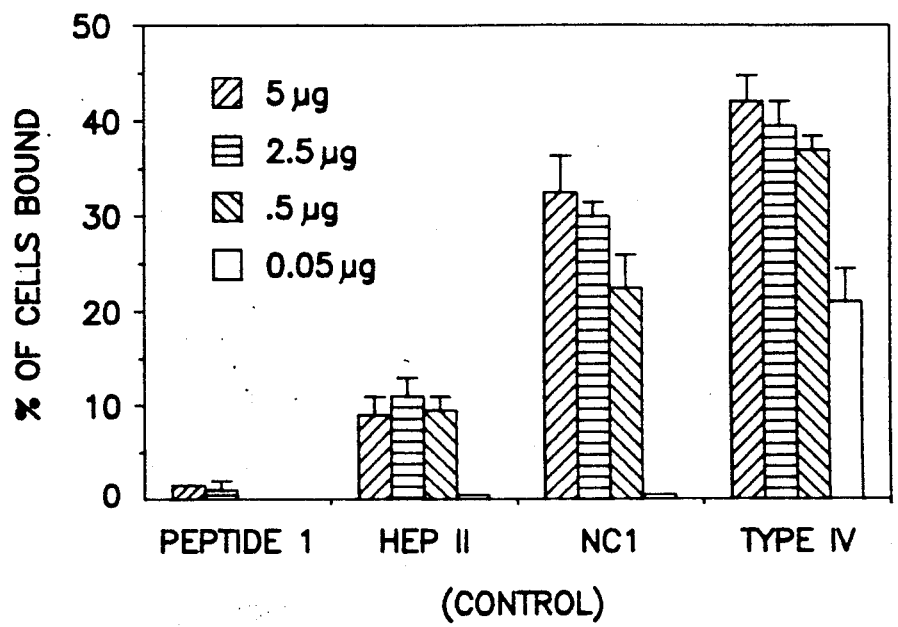
FIG. 6 is a graph depicting the direct binding of aortic endothelial cells to peptide Hep-II, and control peptides, coated onto plastic at increasing concentrations.

Bovine aortic endothelial cells were isolated according to the following protocol. Aortas were obtained from a local slaughterhouse, washed in cold phosphate buffered saline (PBS) (136 mM NaCl, 2.6 mM KCl, 15.2 mM $Na_2HPO_4$, pH 7.2) and processed within 2 hours. Crude collagenase (CLS III, 125–145 units per mg dry weight, Cooper Biomedical) was used at 2 mg/ml in Dulbecco's modified Eagle's medium (DMEM) (GIBCO). The vessel was clamped at the distal end, filled with the collagenase-PBS solution and digestion was carried out for 10 minutes. The lumenal contents were harvested, followed by the addition of fresh collagenase for two additional 10-minute periods. The enzyme-cell suspensions were added to an equal volume of DMEM containing 10% fetal bovine serum (FBS) to inhibit the enzyme and spun in a centrifuge at 400× g for 10 minutes. The resulting cell pellet was resuspended in DMEM containing 10% FBS, 100 units/ml of penicillin G, 100 μg/ml of streptomycin and 100 μg/ml of crude fibroblast growth factor. Cells are cultured in 75 $cm^2$ flasks in a humidified 5% $CO_2$ atmosphere at 37° C. Cultures were fed twice a week with the same medium and cells were used in assays when approximately 75% confluent. The cells were labeled for 24 hours prior to use with a mixture of $^{35}$S-labeled amino acids (3 mCi). Cells were identified as endothelial in nature by characteristic cobblestone morphology, contact inhibition of growth upon reaching confluency, and positive immunofluorescent staining for factor VIII:RAg (Miles Laboratories) [Schwartz, In Vitro, 14, 966 (1978)]. Only endothelial cells, megakaryocytes and platelets are known to contain the factor VIII:RAg. This method routinely gives a high yield of endothelial cells with little contamination (less than 5%) by smooth muscle cells, pericytes or fibroblasts as judged by phase contrast microscopy as well as by immunostaining. Direct adhesion of endothelial cells was performed as follows. Plastic substrates were coated with increasing concentrations of peptide Hep-II and a constant number of $^{35}$S-labeled cells were added per well and they were incubated for 120 min. at 37° C. At the end of the incubation period the wells were washed, bound radioactivity was solubilized by 1% SDS-0.5 N NaOH and quantitated in a Beckman scintillation counter. Peptide Hep-II promotes substantial adhesion of endothelial cells even at very low plating concentrations (0.5 μg/well) (FIG. 6). Endothelial cell adhesion to type IV collagen and the NC1 domain are also shown in comparison. BSA and a control peptide (peptide 1, formula NPLCPPGTKIL) did not show any significant adhesion.

B. Inhibition of Adhesion of Bovine Aortic Endothelial Cells to Type IV Collagen by Peptide Hep-II Inhibition of adhesion was measured using 96-well microtiter plates. In each well 50 μl of a type IV collagen solution at 60 μg/ml were absorbed by incubating overnight at 29° C.

Figure 7:
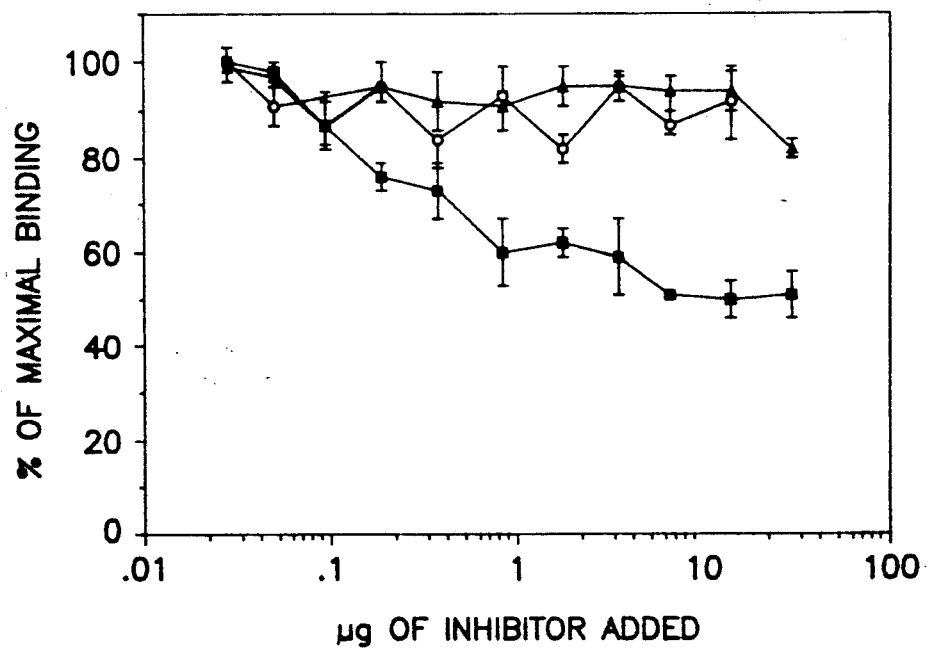
FIG. 7 is a graph depicting the competition of the binding of endothelial cells, to type IV collagen coated substrata in the presence of peptide Hep-II (■), and control peptides 1 (°) and 14 (▲), in solution at increasing concentrations.

Cultures of cells which were 60-80% confluent were metabolically labeled for 24 hours with the addition of 3 mCi/ml of $^{35}$S-amino acid mixture. On the day of assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells were adjusted to a concentration of $3-4\times10^4$/ml, and 50 μl of this cell suspension was added to 50 μl of increasing concentrations of peptide Hep-II in the same buffer at 37° C. After 15 min. of co-incubation, 50 μl of the mixture was applied to the type IV collagen coated wells for 20 min. at 37° C. At the end of the incubation, the wells were washed with warm PBS containing 10 mM Ca++, and the adherent population was solubilized with 0.5 N NaOH containing 1% sodium dodecyl sulfate. The solubilized cells were then quantitated using a liquid scintillation counter. Each determination was done in triplicate. The results of this study are summarized in FIG. 7. Two control peptides, peptide 1 (formula NPLCPPGTKIL) and peptide 14 (formula GEKGDKGLPGLD), could not compete for the binding of endothelial cells to type IV collagen (FIG. 7).

EXAMPLE 5

A. Direct Binding of $^{125}$I-Labeled Peptide Hep-II to Cell Surfaces

Figure 8:
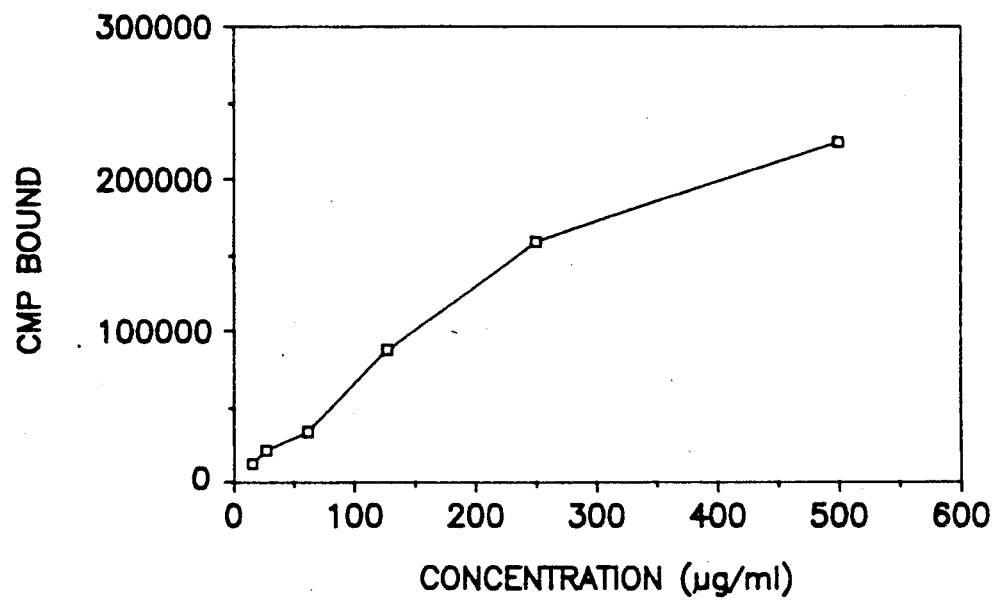
FIG. 8 is a graph depicting the direct binding of increasing concentrations of iodinated ($^{125}$I-labeled) peptide Hep-II to the surface of endothelial cells.

Endothelial cells were grown in culture as described in example 4 (supra). Cells used for this type of experiment were not labeled with radioactivity. Unlabeled cells were harvested by trypsinization (supra) on the day of the experiment. About 5,000 cells were mixed with 50 μl of a given concentration of peptide Hep-II in solution. Increasing concentrations of peptide Hep-II were used. The cells were incubated with the iodinated peptide for 15 min. at 4° C. and they were then pelleted by centrifugation. The cells were then resuspended and washed 3 times with DMEM containing 2 mg/ml BSA and 50 mM Hepes. Following the washes, the cells were pelleted for a final time in plastic tubes, the supernatant was decanted and the radioactivity of the pellet was quantitated in a Beckman scintillation counter. The binding of peptide Hep-II to endothelial cells is saturable (FIG. 8)——an indication of specificity. These experiments indicate that peptide Hep-II specifically interacts with the surfaces of endothelial cells.

Figure 9:
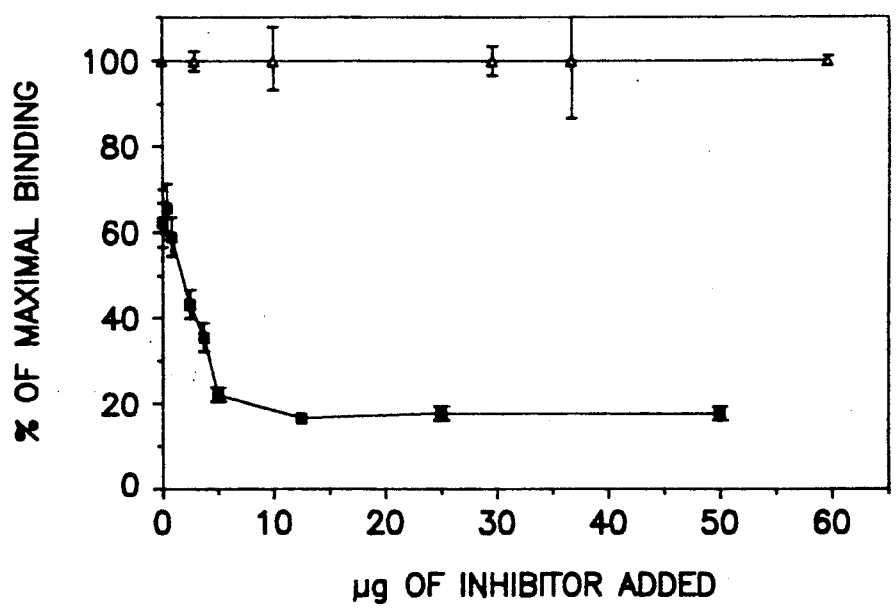
FIG. 9 is a graph depicting the competition of the binding of iodinated peptide Hep-II (■), and control peptide ET-2 (△), to endothelial cells in the presence of increasing concentrations of unlabeled Hep-II and two control peptides.

B. Inhibition of the Binding of $^{125}$I-Labeled Peptide Hep-II to the Cell Surface by an Excess of Unlabeled Peptide Endothelial cells were grown in culture as discussed in examples 4 and 5A (supra). On the day of the experiment, the cells were harvested by trypsinization (supra) and were co-incubated with 50 μl of peptide Hep-II. 50 μl a constant amount of $^{125}$I-labeled peptide Hep-II was mixed with increasing concentrations of unlabeled peptide Hep-II or a control peptide (maximal excess of unlabeled peptide: 500-fold over radiolabeled Hep-II). 50 μl of each concentration of unlabeled peptide which was mixed with radiolabeled Hep-II were then added to cells in suspension (5,000 cells per concentration of peptide). The cells were incubated with the mixture of unlabeled-radiolabeled peptide for 15 min. at 4° C. and they were then pelleted. The cells were subsequently washed and bound radioactivity was quantitated as described in example 4. FIG. 9 shows that the binding of radiolabeled Hep-II to the surface of endothelial cells can be competed only by an excess of unlabeled peptide Hep-II, whereas control (negative) peptide ET-2 (formula GDSRTITTKGERGQP) failed to compete. These experiments provide confirmation that a specific interaction occur between endothelial-cell surfaces and peptide Hep-II.

These results taken together indicate that peptide Hep-II is a major participant in the process of endothelial cell adhesion.

A number of practical applications for the polypeptides of the present invention can be envisioned. Such applications include the promotion of the healing of wounds caused by the placement of synthetic substrata within the body. Such synthetic substrata can include artificial vessels, intraocular contact lenses, hip replacement implants and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel, heart valve or vascular graft, which is generally woven or knitted from nitrocellulose or polyester fiber, particularly Dacron TM (polyethylene terephthalate) fiber. Most types of cells are attracted to type IV collagen and to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumas, e.g., spinal cord injuries.

In such cases, it may be advantageous to couple the peptide to a biological molecule, such as collagen, a glycosaminoglycan or a proteoglycan. It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Also, the polypeptides of the present invention can be used to promote cell adhesion of various cell types to naturally occurring or artificial substrata intended for use in vitro. For example, a culture substrate such as the wells of a microtiter plate or the medium contacting surface of microporous fibers or beads, can be coated with the cell-attachment polypeptides. This can obviate the use of type IV collagen in the medium, thus providing better defined conditions for the culture as well as better reproducibility.

As one example of commercial use of cell attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of coating protein in the growth medium and the present polypeptides are expected to provide an improved, chemically defined coating for such purposes. Other surfaces or materials may be coated to enhance attachment, such as glass, agarose, synthetic resins or long-chain polysaccharides.

In the past, selected laminin domains have been studied for ability to decrease the metastatic potential of invasive cell lines [McCarthy et al., *Cancer Met. Rev.*, 4, 125-152 (1985)]. This effect is mediated via the saturation and therefore neutralization of cell surface receptors for laminin. In accordance with the present invention, the data presented herein suggest that receptors for the polypeptide Hep-II from type IV collagen should exist on cell surfaces of malignant cells. Consequently, this polypeptide could be used to block type IV collagen receptors of metastatic cells and therefore reduce their metastatic potential. In addition, peptide Hep-II could be used to enhance reepithelialization of various transplants, like corneal transplants, etc.

The invention has been described with reference to various specific and preferred embodiments and techniques. However, it should be understood that many variations and modifications may be made while remaining within the spirit and scope of the invention.

What is claimed is:

1. A polypeptide of the formula:

leu-ala-gly-ser-cys-leu-ala-arg-phe-ser-thr-met.

2. A prosthetic device designed for placement in vivo, comprising a surface coated with a composition comprising a polypeptide of the formula:

leu-ala-gly-ser-cys-leu-ala-arg-phe-ser-thr-met.

3. The prosthetic device of claim 2, wherein said surface constitutes a portion of a vascular graft.

4. The prosthetic device of claim 2, wherein said surface is made of a synthetic resin fiber.

5. The prosthetic device of claim 2, wherein said surface constitutes a portion of an intraocular contact lens.

6. The prosthetic device of claim 2, wherein said surface constitutes a portion of a hip replacement implant.

7. The prosthetic device of claim 2, wherein said surface constitutes a portion of a percutaneous device.

8. A prosthetic device in accordance with claim 4, wherein said synthetic resin fiber is selected from the group consisting of nitrocellulose or polyester.

9. A prosthetic device in accordance with claim 4, wherein said synthetic resin fiber is a polyethylene terephthalate.

10. A cell culture substrate having a surface coated with a composition comprising a polypeptide of the formula:

leu-ala-gly-ser-cys-leu-ala-arg-phe-ser-thr-met.

11. The cell culture substrate of claim 10, wherein said surface is made of a synthetic resin.

12. The cell culture substrate of claim 10, wherein said surface constitutes a portion of a bead.

13. The cell culture substrate of claim 10, wherein said surface constitutes a portion of a microporous fiber.

14. The cell culture substrate of claim 10, wherein said surface constitutes the wells of a microtiter plate.

* * * * *

UNITED STATES PATENT AND TRADEMARK OFFICE
CERTIFICATE OF CORRECTION

PATENT NO. :    5,081,031
DATED      :    January 14, 1992
INVENTOR(S) :   Photini-Effie C. Tsilibary et al.

It is certified that error appears in the above-identified patent and that said Letters Patent is hereby corrected as shown below:

Col. 4, line 4, for "Ill." read --IL--

At col. 5, line 65, for "3-heparin" read --$^3$H-heparin--

Signed and Sealed this

Eighth Day of February, 1994

Attest:

BRUCE LEHMAN

Attesting Officer    Commissioner of Patents and Trademarks